United States Patent

Furuzawa et al.

[11] Patent Number: 4,493,842
[45] Date of Patent: Jan. 15, 1985

[54] FUNGICIDAL N-(PHENYL-LOWER ALKANOYL-)-IMIDAZOLE DERIVATIVES, COMPOSITION, AND METHOD OF USE

[75] Inventors: Kunihiko Furuzawa, Takarazuka; Yuji Funaki, Toyonaka; Yoshio Hisada, Amagasaki; Kazuo Izumi, Takarazuka, all of Japan

[73] Assignee: Sumitomo Chemical Company, Limited, Osaka, Japan

[21] Appl. No.: 494,349

[22] Filed: May 13, 1983

[30] Foreign Application Priority Data

| May 21, 1982 | [JP] | Japan | 57-87034 |
| May 25, 1982 | [JP] | Japan | 57-89483 |
| Nov. 17, 1982 | [JP] | Japan | 57-202597 |
| Nov. 22, 1982 | [JP] | Japan | 57-205306 |

[51] Int. Cl.³ .................. A01N 43/50; C07D 233/58; C07D 233/60
[52] U.S. Cl. ................................ 424/273 R; 548/341
[58] Field of Search ................. 548/336, 341; 424/273

[56] References Cited

PUBLICATIONS

Staab et al., C.A., vol. 57, p. 5907; 1962.
Chem. Ber., 95, 1275–1283, (1962).

Primary Examiner—Henry R. Jiles
Assistant Examiner—J. G. Mullins
Attorney, Agent, or Firm—Stevens, Davis, Miller & Mosher

[57] ABSTRACT

N-acylimidazole compounds represented by the formula:

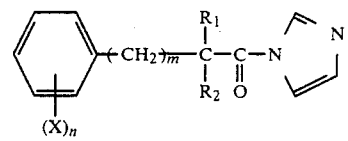

wherein X is halogen atom, or alkyl, alkoxy, lower alkylthio, halogen-substituted alkyl, phenyl, phenoxy, cyano, phenyl lower alkoxy or nitro group, $R_1$ and $R_2$, which may be the same or different, are hydrogen or halogen atom, or alkyl, lower alkenyl, lower alkoxy, trifluoromethyl, lower cycloalkyl lower alkyl or lower alkoxy lower alkyl group, or $R_1$ and $R_2$, taken together, may form lower alkylene or halogen-substituted lower alkylene group, m is 0 or 1, n is 0, 1 or 2, and when n is 2, $(X)_2$ groups may form methylenedioxy group, which compounds are useful for controlling plant-disease, regulating plant growth and controlling weeds.

7 Claims, No Drawings

FUNGICIDAL N-(PHENYL-LOWER ALKANOYL-)-IMIDAZOLE DERIVATIVES, COMPOSITION, AND METHOD OF USE

The present invention relates to N-acylimidazoles represented by the formula:

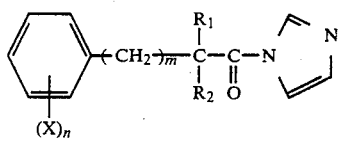

wherein X is halogen atom, or alkyl, alkoxy, lower alkylthio, halogen-substituted alkyl, phenyl, phenoxy, cyano, phenyl lower alkoxy or nitro group, $R_1$ and $R_2$, which may be the same or different, are hydrogen or halogen atom, or alkyl, lower alkenyl, lower alkoxy, trifluoromethyl, lower cycloalkyl lower alkyl or lower alkoxy lower alkyl group, or $R_1$ and $R_2$, taken together, may form lower alkylene or halogen-substituted lower alkylene group, m is 0 or 1, n is 0, 1 or 2, and when n is 2, $(X)_2$ groups may form methylenedioxy group (hereinafter referred to as "present compound(s)"), and to production of these compounds and use of these compounds as plant disease-controlling agents, plant growth-regulating agents or herbicides.

Some kinds of N-acylimidazoles, for example, cinnamoylimidazole and p-chlorobenzoylimidazole, are described in Chem. Ber., 95, 1275 (1962), but there is no description on whether or not these compounds have some physiological activity on plants.

The present inventors made an extensive study on the physiological activity of N-acylimidazoles on plants and as a result, found that the present compounds have a preventive, curative or systemic controlling activity on many plant diseases and a plant growth-regulating activity such as an activity to control the growth of some kinds of crops as well as a herbicidal activity on weeds in paddy fields and plowed fields.

In the present invention, the alkyl and alkoxy groups are those having 12 or less carbon atoms, and the term "lower" means 8 or less carbon atoms. The halogen atom means a fluorine, chlorine, bromine or iodine atom. Further, in the scope of the present compounds, salts of the compound with a plant-physiologically acceptable acid such as inorganic acids (e.g. hydrochloric acid, hydrobromic acid, hydroiodic acid, sulfuric acid, nitric acid, phosphoric acid), carboxylic acids (e.g. acetic acid, trichloroacetic acid, maleic acid, succinic acid) and sulfonic acids (e.g. p-toluenesulfonic acid) as well as optically active compounds thereof are included.

Examples of the plant diseases on which the present compounds have a controlling activity are given below:

Blast of rice (*Pyricularia oryzae*), helminthosporium leaf spot of rice (*Cochliobolus miyabeanus*), sheath blight of rice (*Rhizoctonia solani*), powdery mildew of wheat and barley (*Erysiphe graminis* f. sp. hordei, f. sp. tritici), fusarium blight of wheat and barley (*Gibberella zeae*), rust of wheat & barley (*Puccinia striiformis, P. graminis, P. recondita, P. hordei*), snow blight of wheat & barley (Typhula sp., *Micronectriella nivalis*), loose smut of wheat & barley (*Ustilago tritici, U. nuda*), eye spot of wheat & barley (*Pseudocercosporella herpotrichoides*), leaf blotch of wheat & barley (*Rhynchosporium secalis*), speckled leaf blotch of wheat & barley (*Septoria tritici*), glume blotch of wheat & barley (*Leptosphaeria nodorum*), melanose of citrus (*Diaporthe citri*), scab of citrus (*Elsinoe fawcetti*), fruit rot of citrus (*Penicillium digitatum, P. italicum*), blossom blight of apple (*Sclerotinia mali*), canker of apple (*Valsa mali*), powdery mildew of apple (*Podosphaera leucotricha*), alternaria leaf spot of apple (*Alternaria mali*), scab of apple (*Venturia inaequalis*), scab of pear (*Venturia nashicola*), black spot of pear (*Alternaria kikuchiana*), rust of pear (*Gymnosporangium haraeanum*), brown rot of peach (*Sclerotinia cinerea*), scab of peach (*Cladosporium carpophilum*), phomopsis rot of peach (Phomopsis sp.), anthracnose of graph (*Elsinoe ampelina*), ripe rot of grape (*Glomerella cingulata*), powdery mildew of grape (*Uncinula necator*), rust of grape (*Phakopsora ampelopsidis*), anthracnose of Japanese persimmon (*Gloeosporium kaki*), leaf spot of Japanese persimmon (*Cercospora kaki, Mycosphaerella nawae*), anthracnose of cucumber (*Colletotrichum lagenarium*), powdery mildew of cucumber (*Sphaerotheca fuliginea*), gummy stem blight of cucumber (*Mycosphaerella melonis*), early blight of tomato (*Alternaria solani*) leaf mold of tomato (*Cladosporium fulvum*), phomopsis blight of eggplant (*Phomopsis vexans*), powdery mildew of eggplant (*Erysiphe cichoracearum*), alternaria leaf spot of brassica (*Alternaria japonica*), white spot of brassica (*Cercosporella brassicae*), rust of Welsh onion (*Puccinia allii*), purple stain of soybean (*Cercospora kikuchii*), anthracnose of soybean (*Elsinoe glycines*), melanose of soybean (*Diaporthe phaseolorum* var. sojae), anthracnose of kidney bean (*Colletotrichum lindemuthianum*), leaf spot of peanut (*Mycosphaerella personatum*) brown leaf spot of peanut (*Cercospora arachidicola*), powdery mildew of pea (*Erysiphe pisi*), early blight of potato (*Alternaria solani*), powdery mildew of strawberry (*Sphaerotheca humuli*) net blister blight of tea (*Exobasidium reticulatum*), white scab of tea (*Elsinoe leucospila*), brown spot of tobacco (*Alternaria logipes*), powdery mildew of tobacco (*Erysiphe cichoracearum*), anthracnose of tobacco (*Colletotrichum tabacum*), cercospora leaf spot of beet (*Cerocospora beticola*), scab of rose (*Diplocarpon rosae*), powdery mildew of rose (*Sphaerotheca pannosa*), leaf blight of chrysanthemum (*Septoria chrysanthemiindici*), rust of chrysanthemum (*Puccinia horiana*), gray mold (*Botrytis cinerea*) and stem rot (*Sclerotinia sclerotiorum*) of various crops, and the like. In the scope of crops on which the present compound have a plant growth-regulating activity, broadleaf crops such as soybean, cotton, etc., lawn grass, fruit trees such as apple, citrus, etc., and tobacco are included. Furhter, the present compounds have a height-controlling activity on broadleaf crops such as soybean, cotton, etc., a growth-controlling activity on lawn grass, a waste sprout-controlling activity on fruit trees, an axillary bud-inhibiting activity on tobacco, and the like. Further, of weeds on which the present compounds have a herbicidal activity, weeds present in plowed fields include for example, grassy weeds such as barnyard grass (*Echinochroa crus-galli*), green foxtail (Setaria viridis), large crabgrass (*Digitaria sanguinalis*) etc., broadleaf weeds such as common purslane (*Portulaca oleracea*), chickweed (*Stellaria media*), common lambsquarters (*Chenopodium album*), pigweed (*Amaranthus patulus*), etc., and Cyperaceae family weeds such as rice flatsedge (*Cyperus iria*), purple nutsedge (*Cyperus rotundus*), etc.; and weeds present in paddy fields include, for example, grassy weeds such as barnyard grass (*Echinochroa crus-galli*), etc., broadleaf weeds such as false pimpernel (*Lindernia procumbens*), spike-flowered rotala (*Rotala indica*), long stemmed waterwort (*Elatine triandra*), etc., Cyperaceae family weeds such as smallflower umbrellaplant (*Cyperus defformis*), bulrush (*Scirpus juncoides*), slender spikerush (*Eleocharis acicularis*), water nutgrass (*Cyperus serotinus*), etc., and monochoria (*Monochoria vaginalis*), Japanese ribbon wapato (*Sagittaria pygmaea*), narrow-leaved arrowhead (*Alisma canaliculatum*), etc.

The present compounds therefore, can be used as an active ingredient for plant disease-controlling agents, plant growth-regulating agents or herbicides for use in paddy fields, plowed fields, orchards, tea gardens, pastures, turf and forest as well as in non-cultivated land.

The present compounds can be produced by reacting a carboxylic acid represented by the formula:

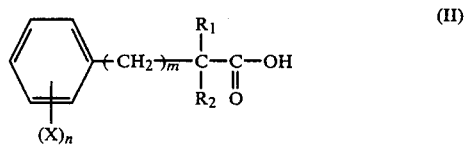

wherein X, $R_1$, $R_2$, m and n are as defined above, or its derivative with 0.5 to 5 equivalents of imidazole or its derivative in a solvent in the presence or absence of 0.95 to 1.1 equivalents of a reaction assistant at $-10°$ C. to $150°$ C., preferably $0°$ C. to $120°$ C., for 0.5 to 24 hours.

The solvent includes, for example, hydrocarbons (e.g. hexane, heptane, ligroin, benzene, toluene), halogenated hydrocarbons (e.g. chloroform, carbon tetrachloride, dichloroethane, chlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone), esters (e.g. ethyl acetate, butyl acetate), nitriles (e.g. acetonitrile, isobutyronitrile), tetriary amines (e.g. pyridine, triethylamine, N,N-diethylaniline, N-methylmorpholine), acid amides (e.g. N,N-dimethylformamide, acetamide), sulfur compounds (e.g. dimethylsulfoxide, sulforan) and mixtures thereof.

The derivative of the carboxylic acid includes for example acid anhydrides, acid chlorides, acid bromides and the like, and that of imidazole includes for example carbonyl diimidazole, thionyl diimidazole, sodium or potassium salt of imidazole and the like.

As the reaction assistant, dehydrating agents such as dicyclohexylcarbodiimide, phosphorus trichloride, thionyl chloride, etc. are used for reaction between the carboxylic acid and imidazole, and for reaction between the acid chloride or acid bromide of the carboxylic acid and imidazole, acid-binding agents such as inorganic bases (e.g. sodium hydroxide, potassium hydroxide, sodium carbonate, potassium carbonate, sodium hydrogen-carbonate), organic bases (e.g. pyridine, triethylamine, N,N-diethylaniline, N-methylmorpholine), carboxylic acid salts (e.g. sodium acetate, potassium acetate) and the like are used.

After completion of the reaction, usual after-treatments are applied, and if necessary, purification is carried out by chromatography, recrystallization and the like.

The carboxylic acid represented by the formula (II), a starting material for producing the present compounds is produced according to the method described in Tetrahedron, 36, 775 (1980) and Israel J. Chem., 5, 223 (1967).

Examples of methods for producing the present compounds will now be illustrated.

PRODUCTION EXAMPLE 1

To 30 ml of dry tetrahydrofuran was added 1.0 g of carbonyl diimidazole, and 1.3 g of α-benzyl-tert-butylacetic acid was then added at room temperature. Thereafter, the mixture was heated under reflux for 4 hours and concentrated under reduced pressure. The oily product obtained was purified by column chromatography on silica gel to obtain 0.96 g of N-(α-benzyl-tert-butylacetyl)imidazole (compound No. 1). m.p. 90°–91° C.

PRODUCTION EXAMPLE 2

To 30 ml of acetonitrile were added 0.75 g of imidazole and 1.2 g of triethylamine, and 3.0 g of α-(p-bromobenzyl)-tert-butyl-acetic acid chloride was then added dropwise at room temperature. Thereafter, the mixture was stirred at room temperature for 6 hours, poured into 300 ml of water and extracted with 300 ml of chloroform. The extract was dried over anhydrous sodium sulfate and concentrated under reduced pressure. The oily product obtained was recrystallized from diisopropyl ether to obtain 2.39 g of N-[α-(p-bromobenzyl)-tert-butylacetyl]imidazole (compound No. 4). m.p. 101°–102° C.

PRODUCTION EXAMPLE 3

To 20 ml of acetonitrile was added 2.3 g of the sodium salt of imidazole, and 7.0 g of α-methoxy-α-n-propyl-2,4-dichlorophenylacetic acid chloride was then added dropwise at room temperature. The mixture was stirred for 2 hours, poured into 200 ml of ice water and extracted with 300 ml of chloroform. The extract was concentrated under reduced pressure, and the oily product obtained was purified by column chromatography on silica gel to obtain 2.5 g of N-(α-methoxy-α-n-propyl-2,4-dichlorophenylacetyl)imidazole (compound No. 43). m.p. 99°–101° C.

PRODUCTION EXAMPLE 4

To 20 ml of dry tetrahydrofuran was added 1.6 g of thionyl diimidazole, and 2.0 g of α-(p-methoxybenzyl)-tert-butylacetic adie was then added at room temperature. The mixture was stirred for 6 hours and concentrated under reduced pressure. The oily product obtained was purified by column chromatography on silica gel to obtain 0.31 g of N-[α-(p-methoxybenzyl)-tert-butylacetyl]-imidazole (compound No. 49). m.p. 89.5°–91° C.

Some of the present compounds which can be produced by this type of production method are shown in Table 1.

TABLE 1

N—acylimidazole represented by the formula:

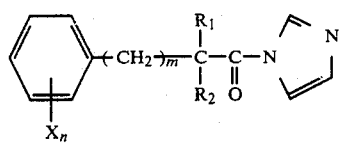

| Compound No. | $X_n$ | m | $R_1$ | $R_2$ | Physical constant |
|---|---|---|---|---|---|
| 1 | H | 1 | t-$C_4H_9$ | H | mp 90–91° C. |
| 2 | 4-F | 1 | " | H | $n_D^{24}$ 1.5223 |
| 3 | 4-Cl | 1 | " | H | mp 100–101° C. |
| 4 | 4-Br | 1 | " | H | mp 101–102° C. |
| 5 | 4-I | 1 | " | H | mp 112–113° C. |
| 6 | 2,4-$Cl_2$ | 0 | $CH_3$ | $CH_3$ | $n_D^{22}$ 1.5705 |
| 7 | " | 0 | " | $C_2H_5$ | $n_D^{25}$ 1.5711 |
| 8 | " | 0 | " | n-$C_3H_7$ | $n_D^{27}$ 1.5650 |
| 9 | " | 0 | " | i-$C_4H_9$ | $n_D^{28}$ 1.5480 |
| 10 | " | 0 | " | $CH_3OCH_2$ | $n_D^{23}$ 1.5539 |
| 11 | " | 0 | " | $C_2H_5OCH_2$ | $n_D^{26}$ 1.5420 |
| 12 | " | 0 | $C_2H_5$ | $C_2H_5$ | $n_D^{24}$ 1.5439 |
| 13 | " | 0 | " | $CH_3OCH_2$ | $n_D^{25}$ 1.5585 |
| 14 | " | 0 | —$(CH_2)_3$— | | $n_D^{25}$ 1.5865 |
| 15 | " | 0 | —$(CH_2)_5$— | | $n_D^{23}$ 1.5705 |
| 16 | " | 0 | —$CH_2CH_2$—$C(CH_3)_2$—$CH_2$— | | mp 130–131° C. |
| 17 | " | 0 | —$CH_2CH_2$—$CH(n-C_3H_7)CH_2$— | | $n_D^{26}$ 1.5639 |
| 18 | 2-F | 0 | —$(CH_2)_4$— | | mp 67–68° C. |
| 19 | 2-Cl | 0 | " | | $n_D^{22}$ 1.5745 |
| 20 | 2-Br | 0 | " | | mp 84–85° C. |
| 21 | 2-$CH_3$ | 0 | " | | $n_D^{27}$ 1.5690 |
| 22 | 2-$CH_3O$ | 0 | " | | mp 90–91° C. |
| 23 | 3-Cl | 0 | " | | $n_D^{23}$ 1.5725 |
| 24 | 4-Cl | 0 | " | | $n_D^{24}$ 1.5605 |
| 25 | 4-$CH_3O$ | 0 | " | | $n_D^{25}$ 1.5610 |
| 26 | 2,5-$(CH_3)_2$ | 0 | " | | $n_D^{27}$ 1.5649 |
| 27 | 2-$CF_3$ | 0 | " | | $n_D^{27}$ 1.5225 |
| 28 | 2,5-$Cl_2$ | 0 | " | | mp 143–144° C. |
| 29 | 2-Cl | 0 | $CH_3$ | $CH_3$ | mp 99–100° C. |
| 30 | 2-Cl | 0 | $CH_3$ | $C_2H_5$ | mp 114–115° C. |
| 31 | 2-Cl | 0 | $CH_3$ | $CH_3OCH_2$ | mp 103–104° C. |
| 32 | 4-Cl | 0 | $CH_3$ | $C_2H_5$ | $n_D^{22}$ 1.5575 |
| 33 | H | 0 | $CH_3$ | $CH_3$ | $n_D^{25}$ 1.5540 |
| 34 | H | 0 | $CF_3$ | $CH_3O$ | $n_D^{26}$ 1.5050 |
| 35 | 2,4-$Cl_2$ | 0 | $CH_3$ | $CH_3O$ | $n_D^{27}$ 1.5565 |
| 36 | 2-Cl, 4-F | 0 | —$(CH_2)_4$— | | mp 69–70° C. |
| 37 | 2,4-$Cl_2$ | 0 | $CH_3$ | $CH_2$=$CHCH_2$ | $n_D^{26}$ 1.5730 |
| 38 | 2-Cl | 0 | $CH_3$ | $CH_3O$ | $n_D^{27}$ 1.5462 |
| 39 | 2-Cl | 0 | n-$C_3H_7$ | $CH_3O$ | mp 134–135° C. |
| 40 | H | 0 | —$(CH_2)_5$— | | mp 95–96° C. |
| 41 | 4-Cl | 0 | —$(CH_2)_3$— | | mp 104–105° C. |
| 42 | 2-Br | 0 | $CH_3$ | $CH_3$ | $n_D^{25}$ 1.5751 |
| 43 | 2,4-$Cl_2$ | 0 | n-$C_3H_7$ | $CH_3O$ | mp 99–101° C. |
| 44 | " | 0 | $CH_3$ | n-$C_6H_{13}$ | $n_D^{24}$ 1.5470 |
| 45 | " | 0 | $CH_3$ | Br | $n_D^{26}$ 1.5905 |
| 46 | 4-$CH_3$ | 1 | t-$C_4H_9$ | H | mp 115–116° C. |
| 47 | 4-$C_2H_5$ | 1 | " | H | mp 50–52° C. |
| 48 | 4-t-$C_4H_9$ | 1 | " | H | mp 99–100° C. |
| 49 | 4-$CH_3O$ | 1 | " | H | mp 89.5–91° C. |
| 50 | 4-$C_6H_5$ | 1 | " | H | mp 145–146° C. |
| 51 | 4-CN | 1 | " | H | mp 119–120.5° C. |
| 52 | 4-$C_2H_5O$ | 1 | " | H | mp 88.5–90° C. |
| 53 | 4-$C_6H_5CH_2O$ | 1 | " | H | mp 118–119° C. |
| 54 | 4-i-$C_3H_7$ | 1 | " | H | mp 75–76° C. |
| 55 | 4-n-$C_3H_7O$ | 1 | " | H | $n_D^{22}$ 1.5297 |
| 56 | 4-n-$C_4H_9O$ | 1 | " | H | mp 58–59° C. |
| 57 | 2-Cl | 1 | " | H | mp 87–88.5° C. |
| 58 | 3-Cl | 1 | " | H | mp 100–101° C. |
| 59 | 2,4-$Cl_2$ | 1 | " | H | mp 117–118° C. |
| 60 | 3,4-$Cl_2$ | 1 | " | H | mp 104–105° C. |
| 61 | 3-$CF_3$ | 1 | " | H | $n_D^{25}$ 1.4920 |
| 62 | 2,6-$Cl_2$ | 1 | " | H | $n_D^{25}$ 1.5400 |
| 63 | 2-$CH_3$ | 1 | " | H | mp 71.5–73° C. |
| 64 | 3-$CH_3$ | 1 | " | H | mp 74.5–76° C. |
| 65 | 2-Br | 1 | " | H | mp 79–80.5° C. |
| 66 | 3-F | 1 | " | H | $n_D^{14}$ 1.5157 |
| 67 | 3-$CH_3O$ | 1 | " | H | mp 101.5–102.5° C. |
| 68 | 3-I | 1 | " | H | mp 85–86° C. |
| 69 | 4-$CF_3$ | 1 | " | H | mp 72–73° C. |
| 70 | 4-$NO_2$ | 1 | " | H | mp 86.5–88° C. |
| 71 | 2,4-$Cl_2$ | 0 | —$(CH_2)_2$— | | mp 102–103° C. |

TABLE 1-continued

N—acylimidazole represented by the formula:

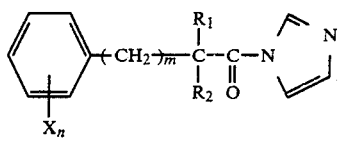

| Compound No. | $X_n$ | m | $R_1$ | $R_2$ | Physical constant |
|---|---|---|---|---|---|
| 72 | " | 0 | $CH_3$ | $CH_2=CHCH_2$ | $n_D^{22}$ 1.5682 |
| 73 | " | 0 | $CH_3$ | cyclopropyl-$CH_2$ | $n_D^{25}$ 1.5752 |
| 74 | " | 0 | —$CH_2$—$CCl_2$— | | $n_D^{20}$ 1.5890 |
| 75 | 2-Cl | 0 | —$(CH_2)_2$— | | $n_D^{22}$ 1.5750 |
| 76 | 4-Cl | 0 | —$CH_2$—$CCl_2$— | | $n_D^{23}$ 1.5511 |
| 77 | 3,4-$(CH_3O)_2$ | 1 | $t$-$C_4H_9$ | H | mp 134–135.5° C. |
| 78 | 4-Cl | 0 | $t$-$C_4H_9CH_2$ | H | mp 167–168° C. |
| 79 | 4-$s$-$C_4H_9O$ | 1 | $t$-$C_4H_9$ | H | mp 73–74° C. |
| 80 | 4-$C_6H_5O$ | 1 | $t$-$C_4H_9$ | H | $n_D^{25}$ 1.5537 |
| 81 | 4-$n$-$C_6H_{13}O$ | 1 | $t$-$C_4H_9$ | H | $n_D^{25}$ 1.5125 |
| 82 | 4-$n$-$C_8H_{17}O$ | 1 | $t$-$C_4H_9$ | H | $n_D^{23}$ 1.5187 |
| 83 | 4-Br | 1 | $C_2H_5C(CH_3)_2$ | H | $n_D^{27}$ 1.5453 |
| 84 | 3-CN | 1 | $t$-$C_4H_9$ | H | mp 123–124.5° C. |
| 85 | 3,4-$OCH_2O$— | 1 | $t$-$C_4H_9$ | H | mp 108–109.5° C. |
| 86 | 2,4-$Cl_2$ | 0 | —$(CH_2)_4$— | | $n_D^{22.5}$ 1.5790 |
| 87 | 2-F | 1 | $t$-$C_4H_9$ | H | mp 99.5–100.5° C. |
| 88 | 4-Cl | 1 | $t$-$C_4H_9CH_2$ | H | mp 123–124° C. |
| 89 | 2-$CH_3O$ | 1 | $t$-$C_4H_9$ | H | $n_D^{25}$ 1.5738 |
| 90 | 3-$CH_3$, 4-$CH_3O$ | 1 | " | H | mp 100.5–101.5° C. |
| 91 | 3-Br | 1 | " | H | mp 103–104° C. |
| 92 | 4-Cl | 1 | $s$-$C_4H_9$ | H | $n_D^{23}$ 1.5454 |
| 93 | 4-$CH_3S$ | 1 | $t$-$C_4H_9$ | H | mp 96–97° C. |
| 94 | 4-$C_6H_5O$ | 1 | " | H | $n_D^{25}$ 1.5240 |
| 95 | 4-$i$-$C_4H_9O$ | 1 | " | H | mp 96.5–98° C. |

When the present compounds are used as an active ingredient for plant disease-controlling agents, plant growth-regulating agents or herbicides, they may be used as such without adding any other components. Generally, however, they are mixed with solid or liquid carriers, surfactants and some other assistants for formulation in preparing their compositions such as emulsifiable concentrates, wettable powders, suspensions, granules, dusts, water-soluble formulations, oil sprays and the like.

These compositions contain 0.1 to 99.9% by weight, preferably 0.2 to 80% by weight of the present compounds as an active ingredient.

The solid carrier includes, for example, fine powders or powdery products of kaolin clay, attapulgite clay, bentonite, terra abla, pyrophyllite, talc, diatomaceous earth, calcite, corn stalk powder, walnut powder, urea, ammonium sulfate, synthetic hydrated silicon dioxide and the like. The liquid carrier includes, for example, aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethylsulfoxide, acetonitrile, water and the like.

As the surfactant used for the purposes of emulsification, dispersion, wetting and the like, there are given, for example, anionic surfactants such as salts of alkyl sulfate, alkyl(aryl)sulfonates, dialkylsulfosuccinates, salts of phosphoric acid esters of polyoxyethylene alkylaryl ether, naphthalenesulfonic acid/formalin condensates, etc., and nonionic surfactants such as polyoxyethylene alkyl ether, polyoxyethylene polyoxypropylene block copolymers, sorbitan fatty acid esters, polyoxyethylene sorbitan fatty acid esters, fatty acid/polyoxyethylene adducts, etc. The assistant for formulation includes, for example, lignosulfonates, alginates, polyvinyl alcohol, gum arabic, CMC (carboxymethyl cellulose), PAP (acid isopropyl phosphate), etc.

Formulation examples will be shown in the following examples. In the examples, the present compounds are shown by a compound number in Table 1, and part means part by weight.

FORMULATION EXAMPLE 1

Fifty parts of the compund (4), 3 parts of calcium lignosulfonate, 2 parts of sodium lauryl sulfate and 45 parts of synthetic hydrated silicon oxide are well mixed with pulverizing to obtain a wettable powder.

FORMULATION EXAMPLE 2

Ten parts of the compound (6), 14 parts of polyoxyethylene styrylphenyl ether, 6 parts of calcium dodecylbenzenesulfonate, 55 parts of xylene and 15 parts of a fatty acid/polyoxyethylene adduct are well mixed to obtain an emulsifiable concentrate.

FORMULATION EXAMPLE 3

Two parts of the compound (37), 1 part of synthetic hydrated silicon oxide, 2 parts of calcium lignosulfonate, 30 parts of bentonite and 65 parts of kaolin clay are well mixed with pulverizing. The mixture is well kneaded with water, granulated and dried to obtain a granule.

FORMULATION EXAMPLE 4

Twenty-five parts of the compound (49), 3 parts of polyoxyethylene sorbitan monooleate, 3 parts of CMC and 69 parts of water are mixed and wet-pulverized until the particle size of the active ingredient is 5 microns or less. A suspension is thus obtained.

FORMULATION EXAMPLE 5

Two parts of the compound (51), 88 parts of kaolin clay and 10 parts of talc are well mixed with pulverizing to obtain a dust.

FORMULATION EXAMPLE 6

Ten parts of the compound (73), 1 part of polyoxyethylene styrylphenyl ether and 89 parts of water are mixed to obtain a water-soluble formulation.

These compositions as such or after diluted with water, are applied to foliage or soil. In application to the soil, the compositions are sprayed onto soil surface (as need arises, they are mixed with the soil after spraying), or soil is drenched with them. Further, by using these compositions together with other plant disease-controlling agents, improvement in the controlling activity of the compositions can be expected. The compositions can also be used in mixture with other plant growth-regulating agents, other herbicides, insecticides, acaricides, nematocides, fertilizers, soil improvers and the like.

When the present compounds are used as an active ingredient for plant disease-controlling agents, plant growth-regulating agents or herbicides, the dosage rate is generally 1 to 500 g/are, preferably 10 to 250 g/are. When emulsifiable concentrates, wettable powders, suspensions, water-soluble formulations, etc. are used in dilution with water, the application concentration is 0.01 to 100%, preferably 0.05 to 5%. Granules, dusts, oil sprays, etc. are applied as such without dilution.

Test examples on the plant disease-controlling activity, plant growth-regulating activity and herbicidal activity of the present compounds will be shown in the following examples. The present compounds are shown by a compound number in Table 1, and compounds used as a control are shown by a compound symbol in Table 2.

TABLE 2

| Compound symbol | Chemical structure | Remark |
| --- | --- | --- |
| A | 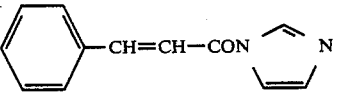 | Compound described in Chem. Ber., 95, 1275 (1962). |
| B | 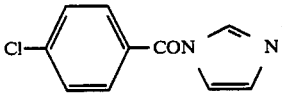 | Compound described in Chem. Ber., 95, 1275 (1962). |
| C | 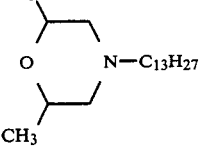 | Tridemorph (well-known fungicide) |
| D | 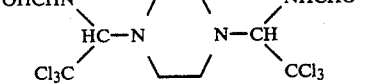 | Triforine (well-known fungicide) |
| E | 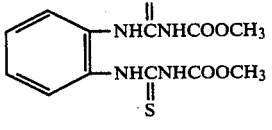 | Thiophanate methyl (well-known fungicide) |
| F | 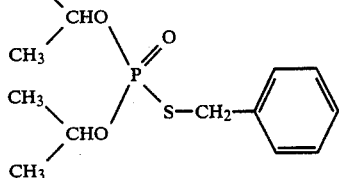 | IBP (well-known fungicide) |

The plant disease-controlling activity is shown by control of disease which is calculated from disease severity obtained as follows: First, the disease appearance, i.e. percentage of infected area, of the leaves of test plants on examination is examined with the naked eye, and its degree is graded in terms of disease index,

| Disease index | |
|---|---|
| 0 | No infected area is observed on leaf surface. |
| 1 | About 5% of infected area is observed. |
| 2 | About 20% of infected area is observed. |
| 4 | About 50% of infected area is observed. |
| 8 | More than 50% of infected area is observed which is not different from the disease appearance in untreated plot. |

Disease severity is then calculated from the equation:

$$\text{Disease severity (\%)} = \frac{\Sigma\left\{(\text{disease index}) \times \binom{\text{number of examined}}{\text{leaves}}\right\}}{(\text{number of total examined leaves}) \times 8} \times 100$$

Control of disease:

$$\text{Control of disease (\%)} = \frac{\binom{\text{disease severity}}{\text{in untreated plot}} - \binom{\text{disease severity}}{\text{in treated plot}}}{(\text{disease severity in untreated plot})} \times 100$$

The plant growth-regulating activity, for example an activity to inhibit the axillary bud of tobacco, is shown by an axillary bud controlling rate obtained as follows: The fresh weight of axillary buds of tobacco on examination is measured, and an axillary bud controlling rate (%) is obtained from the equation:

$$\text{Axillary bud Controlling rate (\%)} = \left(1 - \frac{\text{fresh weight of axillary buds per tobacco plant in treated plot}}{\text{fresh weight of axillary buds per tobacco plant in untreated plot}}\right) \times 100$$

The herbicidal activity is shown by grades 0, 1, 2, 3, 4, 5, obtained as follows: The degrees of germination and growth inhibition of test plants on examination are examined with the naked eye and graded as follows:

| Grade | |
|---|---|
| 0 | Not or little different from untreated plot. |
| 1 | |
| 2 | Zone between two limits 0 and 5 is divided into 4 stages. |
| 3 | |
| 4 | |
| 5 | Test plants are not killed or their growth is not disturbed at all. |

TEST EXAMPLE 1

Controlling test on powdery mildew of barley (*Erysiphe graminis* f. sp. hordei, f. sp. tritici) (preventive effect)

Sandy loam was filled in a plastic pot, and barley (var. Akashinriki) was sowed. At the two-leaf stage, the wettable powder of a test compound formulated according to Formulation Example 1, as diluted with water to an application concentration of 200 ppm, was sprayed onto the foliage so that the spray liquor was thoroughly attached to the test plant. After the plant was cultivated in a greenhouse for one day after spraying, it was inoculated by spraying the spore suspension of the powdery mildew fungi. After inoculation, the test plant was cultivated for 10 days at 23° C. in a highly humid condition to examine the controlling activity. The result is shown in Table 3.

TABLE 3

| Test compound | Control of disease |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 98 |
| 13 | 100 |
| 14 | 100 |
| 15 | 100 |
| 16 | 100 |
| 17 | 100 |
| 18 | 95 |
| 19 | 100 |
| 20 | 93 |
| 21 | 97 |
| 22 | 100 |
| 23 | 100 |
| 24 | 100 |
| 25 | 100 |
| 26 | 100 |
| 27 | 100 |
| 28 | 100 |
| 29 | 96 |
| 30 | 98 |
| 31 | 93 |
| 32 | 90 |
| 33 | 96 |
| 34 | 100 |
| 35 | 98 |
| 36 | 100 |
| 37 | 100 |
| 38 | 100 |
| 39 | 100 |
| 40 | 98 |
| 41 | 99 |
| 42 | 100 |
| 43 | 100 |
| 44 | 100 |
| 45 | 97 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 98 |
| 60 | 100 |
| 61 | 97 |
| 62 | 100 |
| 63 | 100 |
| 64 | 100 |
| 65 | 100 |
| 66 | 100 |
| 67 | 100 |
| 68 | 100 |
| 69 | 100 |
| 70 | 100 |
| 71 | 98 |
| 72 | 100 |
| 73 | 100 |
| 74 | 99 |
| 75 | 100 |
| 76 | 100 |
| 77 | 100 |

TABLE 3-continued

| Test compound | Control of disease |
| --- | --- |
| 78 | 90 |
| 79 | 100 |
| 80 | 100 |
| 81 | 100 |
| 82 | 93 |
| 83 | 100 |
| 84 | 100 |
| 85 | 100 |
| 86 | 100 |
| 87 | 98 |
| 88 | 93 |
| 89 | 90 |
| 90 | 100 |
| 91 | 100 |
| 92 | 90 |
| 93 | 98 |
| 94 | 100 |
| 95 | 100 |
| A | 0 |
| B | 0 |
| C | 83 |

TEST EXAMPLE 2

Controlling test on net blotch of barley
(*Helminthosporium teres*) (preventive effect)

Sandy loam was filled in a plastic pot, and barley (var. Akashinriki) was sowed. At the two-leaf stage, the suspension of test compound formulated according to Formulation example 4, as diluted with water to an application concentration of 200 ppm, was sprayed onto the foliage so that the spray liquor was thoroughly attached to the test plant. After the plant was cultivated in a greenhouse for one day after spraying, it was inoculated by spraying the spore suspension of the net blotch fungi. After inoculation, the test plant was cultivated for 10 days at 23° C. in a highly humid condition to examine the controlling activity. The result is shown in Table 4.

TABLE 4

| Test compound | Control of disease |
| --- | --- |
| 3 | 83 |
| 4 | 88 |
| 7 | 74 |
| 15 | 77 |
| 24 | 79 |
| 27 | 82 |
| 37 | 86 |
| 44 | 76 |
| 46 | 83 |
| 49 | 75 |
| 51 | 82 |
| 55 | 83 |
| 60 | 84 |
| 64 | 87 |
| 67 | 90 |
| 69 | 88 |
| 70 | 80 |
| 71 | 91 |
| 74 | 72 |
| 85 | 88 |
| 86 | 79 |
| D | 73 |

TEST EXAMPLE 3

Controlling test on speckled leaf blotch of wheat
(*(Septoria tritici)* (preventive effect)

Sandy loam was filled in a plastic pot, and wheat (var. Norin No. 73) was sowed. At the two-leaf stage, the suspension of test compound formulated according fo Formulation Example 4, as diluted with water to an application concentration of 200 ppm, was sprayed onto the foliage so that the spray liquor was thoroughly attached to the test plant. After the plant was cultivated in a greenhouse for one day after spraying, it was inoculated by spraying the spore suspension of the speckled leaf blotch fungi. After inoculation, the test plant was cultivated for 10 days at 23° C. in a highly humid condition to examine the controlling activity. The result is shown in Table 5.

TABLE 5

| Test compound | Control of disease |
| --- | --- |
| 3 | 100 |
| 4 | 100 |
| 7 | 96 |
| 15 | 100 |
| 24 | 90 |
| 27 | 100 |
| 37 | 100 |
| 44 | 100 |
| 46 | 100 |
| 49 | 98 |
| 51 | 100 |
| 55 | 96 |
| 60 | 94 |
| 64 | 100 |
| 67 | 98 |
| 69 | 100 |
| 70 | 100 |
| 71 | 100 |
| 74 | 100 |
| 85 | 98 |
| 86 | 96 |
| F | 83 |

TEST EXAMPLE 4

Controlling test on gray mold of cucumber (*Botrytis cinera*) (preventive effect)

Sandy loam was filled in a plastic pot, and cucumber (var. Sagami-hanjiro) was sowed. At the cotyledonous stage, the emulsifiable concentrate of test compound formulated according to Formulation Example 2, as diluted with water to an application concentration of 200 ppm, was sprayed onto the foliage so that the spray liquor was thoroughly attached to the test plant. After the plant was cultivated in a greenhouse for one day after spraying, it was inoculated by spraying the spore suspension of the gray mold fungi. After inoculation, the test plant was cultivated for 10 days at 23° C. in a highly humid condition to examine the controlling activity. The result is shown in Table 6.

TABLE 6

| Test compound | Control of disease |
| --- | --- |
| 3 | 100 |
| 4 | 100 |
| 7 | 100 |
| 15 | 100 |
| 24 | 99 |
| 27 | 100 |
| 37 | 100 |
| 44 | 100 |
| 46 | 100 |
| 49 | 98 |
| 51 | 100 |
| 55 | 100 |
| 60 | 100 |
| 64 | 100 |
| 67 | 96 |
| 69 | 100 |
| 70 | 100 |
| 71 | 100 |
| 74 | 100 |

TABLE 6-continued

| Test compound | Control of disease |
|---|---|
| 85 | 100 |
| 86 | 100 |
| E | 96 |

TEST EXAMPLE 5

Controlling test on gray mold of cucumber (*Botryltis cinerea*) (curative effect)

Sandy loam was filled in a plastic pot, and cucumfer (var. Sagami-hanjiro) was sowed. At the cotyledonous stage, the plant was inoculated by spraying the spore suspension of the gray mold fungi. After inoculation, the plant was cultivated in a greenhouse at 23° C. for 1 day in a highly humid condition, and the emulsifiable concentrate of test compound formulated according to Formulation Example 2, as diluted with water to an application concentration of 200 ppm, was then sprayed onto the foliage so that the spray liquor was thoroughly attached to the test plant. The plant was then cultivated at 23° C. for 4 days after spraying in a highly humid condition to examine the controlling activity. The result is shown in Table 7.

TABLE 7

| Test compound | Control of disease |
|---|---|
| 3 | 84 |
| 4 | 78 |
| 7 | 80 |
| 15 | 82 |
| 24 | 86 |
| 27 | 84 |
| 37 | 88 |
| 44 | 85 |
| 46 | 86 |
| 49 | 85 |
| 51 | 82 |
| 55 | 91 |
| 60 | 81 |
| 64 | 82 |
| 67 | 85 |
| 69 | 88 |
| 70 | 96 |
| 71 | 84 |
| 74 | 84 |
| 85 | 88 |
| 86 | 82 |
| E | 76 |

TEST EXAMPLE 6

Tobacco axillary bud-inhibiting test

Field soil was filled in a 1/2000 are Wagner's pot, and tobacco (var. Hics No. 2) was cultivated at a rate of 1 plant/pot and pinched at a height of about 1 m and just before flowering. The emulsifiable concentrate of test compound formulated according to Formulation Example 2, as diluted with water to a predetermined application concentration, was sprayed onto the foliage of the plant at a rate of 25 ml/pot. After spraying, the plant was cultivated for 10 days in a greenhouse, and the developed axillary buds were cut off and measured for fresh weight. The same procedure was separately carried out to obtain the fresh weight. The average fresh weight of axillary bud per plant was then calculated, and the axillary bud inhibiting activity was examined. Further, phytotoxicity to tobacco was examined with the naked eye. The result is shown in Table 8.

TABLE 8

| Test compound | Application concentration (ppm) | Axillary bud controlling rate (%) | Phytotoxicity to tobacco |
|---|---|---|---|
| 2 | 4000 | 96 | None |
| 3 | 2000 | 100 | None |
| 19 | 4000 | 91 | None |
| 46 | 4000 | 88 | None |
| 51 | 4000 | 97 | None |

TEST EXAMPLE 7

Herbicidal test on weeds in paddy field

Wagner's pots (1/5000 are) were each filled with 1.5 kg of paddy field soil and then brought to a condition of paddy field by filling them with water. Rice plants at the three-leaf stage were transplanted, and the seeds of barnyard grass (*Echinochroa crusgalli*) and bulrush (*Scripus juncoides*) were sowed therein. Thereafter, the wettable powder of test compound formulated according to Formulation Example 1, as diluted with water to a pre-determined dosage rate, was poured to the water surface at a rate of 10 ml/pot. After pouring, the plant was cultivated for 25 days in a greenhouse, and the herbicidal activity on the foregoing sowed plants and spontaneously developed broadleaf weeds were examined. The result is shown in Table 9.

TABLE 9

| Test compound | Dosage rate (g/are) | Barnyard grass | Broadleaf weed | Bulrush |
|---|---|---|---|---|
| 3 | 40 | 4 | 5 | 4 |
| 5 | 80 | 3 | 4 | 3 |
| 16 | 20 | 5 | 5 | 2 |
| 19 | 40 | 5 | 5 | 4 |
| 21 | 40 | 5 | 5 | 5 |
| 26 | 40 | 5 | 5 | 4 |
| 29 | 40 | 5 | 5 | 5 |
| 30 | 40 | 5 | 5 | 5 |
| 46 | 40 | 4 | 5 | 5 |
| 49 | 40 | 2 | 5 | 4 |

What is claimed is:

1. N-acylimidazole represented by the formula:

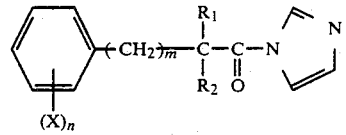

wherein X is halogen atom, or alkyl, alkoxy, lower alkylthio, halogen-substituted alkyl, phenyl, phenoxy, cyano, phenyl lower alkoxy or nitro group, $R_1$ and $R_2$, which may be the same or different, are hydrogen or halogen atom, or alkyl, lower alkenyl, lower alkoxy, trifluoromethyl, lower cycloalkyl lower alkyl or lower alkoxy lower alkyl group, or $R_1$ and $R_2$, taken together, may form lower alkylene or halogen-substituted lower alkylene group, m is 0 or 1, n is 0, 1 or 2, and when n is 2, the $(X)_2$ groups may a form methylenedioxy group.

2. N-[α-(4-chlorobenzyl)-tert-butylacetyl]-imidazole.

3. N-[α-(4-methoxybenzyl)-tert-butylacetyl]-imidazole.

4. N-[α-(4-nitrobenzyl)-tert-butylacetyl]-imidazole.

5. N-(α, α-tetramethylene-2,4-dichlorophenylacetyl)imidazole.

6. A fungicidal composition consisting essentially of a fungicidally effective amount of the compound according to claim 1 and an inert carrier.

7. The method for controlling fungi on plants which consists of applying a fungicidally effective amount of the compound according to claim 1 to the plant.

* * * * *